United States Patent
Su et al.

(10) Patent No.: US 6,704,664 B2
(45) Date of Patent: Mar. 9, 2004

(54) FATIGUE SENSITIVITY DETERMINATION PROCEDURE

(75) Inventors: Hong Su, Windsor (CA); Shang-Rou Hsieh, Ann Arbor, MI (US)

(73) Assignee: Visteon Global Technologies, Inc., Dearborn, MI (US)

( * ) Notice: Subject to any disclaimer, the term of this patent is extended or adjusted under 35 U.S.C. 154(b) by 126 days.

(21) Appl. No.: 10/025,530

(22) Filed: Dec. 18, 2001

(65) Prior Publication Data

US 2003/0114995 A1 Jun. 19, 2003

(51) Int. Cl.[7] .................................................. G01B 3/44
(52) U.S. Cl. ............................. 702/34; 73/577; 73/788; 73/787; 73/808; 73/578
(58) Field of Search ............................ 702/34; 73/577, 73/788, 787, 808, 578

(56) References Cited

U.S. PATENT DOCUMENTS

| | | | |
|---|---|---|---|
| 3,520,180 A | * 7/1970 | Polhemus et al. | 73/670 |
| 3,887,987 A | * 6/1975 | Salt | 29/407.05 |
| 3,957,450 A | * 5/1976 | Salt | 428/544 |
| 4,336,595 A | * 6/1982 | Adams et al. | 702/34 |
| 4,858,146 A | * 8/1989 | Shebini | 703/1 |
| 5,012,428 A | 4/1991 | Ueno et al. | 700/280 |
| 5,047,947 A | 9/1991 | Stump | 700/106 |
| 5,065,618 A | * 11/1991 | Hodges et al. | 73/146 |
| 5,291,419 A | 3/1994 | Satoh et al. | 702/34 |
| 5,565,618 A | 10/1996 | Hu | 73/1.82 |
| 5,767,406 A | 6/1998 | Hu | 73/578 |
| 5,847,259 A | 12/1998 | Hu | 73/1.01 |
| 5,880,362 A | * 3/1999 | Tang et al. | 73/146 |
| 5,965,816 A | 10/1999 | Hu | 73/578 |
| 6,125,333 A | * 9/2000 | Pun | 702/42 |
| 6,141,620 A | * 10/2000 | Zyburt et al. | 701/117 |
| 6,192,745 B1 | * 2/2001 | Tang et al. | 73/146 |
| 6,212,486 B1 | * 4/2001 | Huang et al. | 703/7 |
| 6,564,156 B2 | * 5/2003 | Kuo et al. | 702/34 |

FOREIGN PATENT DOCUMENTS

| | | | | |
|---|---|---|---|---|
| GB | 2 369 209 | * | 5/2002 | |
| GB | 2369209 A | * | 5/2002 | G06F/17/00 |

* cited by examiner

Primary Examiner—John Barlow
Assistant Examiner—Anthony T. Dougherty
(74) Attorney, Agent, or Firm—Brinks Hofer Gilson & Lione

(57) ABSTRACT

A method for determining the sensitivity of the fatigue life of a structural component with respect to specific design parameters includes obtaining the stress profile for a structural component under random process establishing a relationship between the stress profile and the fatigue life of the structural component, developing the sensitivity of the fatigue life with respect to design parameters, optimizing the design of the structural component based upon the design parameters to which the fatigue life is most sensitive.

9 Claims, 2 Drawing Sheets

FATIGUE SENSITIVITY DETERMINATION PROCEDURE

TECHNICAL FIELD OF THE INVENTION

The present invention generally relates to a method of determining the sensitivity of the fatigue life of a structural component with respect to particular design parameters.

BACKGROUND OF THE INVENTION

Fatigue failure is the most common mode of failure for a structural component. Generally, there are three accepted methods of performing fatigue analysis. These methods are stress-life, strain-life and linear elastic fracture mechanics. Among these three, the stress-life (S—N) method is most widely used, particularly in the automotive industry. There has not been a widespread use of the strain-life and linear elastic fracture mechanics methods in the industry, and therefore, there is limited experience and confidence in these methods.

When performing an S—N type fatigue analysis, there are two different approaches. The first approach is a time domain application and the second approach is a frequency domain application. The basic idea in a time domain approach is to apply the rain flow counting process to the fatigue stress history of a structural component to determine the accumulative damage of the structural component. For the frequency domain approach, there is a narrow band method and a wide band method. Both the narrow band and wide band methods of the frequency domain approach simulate the rain flow counting process just as with the time domain approach. However, the frequency domain approach is more efficient, in terms of computer time and resources, due to the simplicity of application and quick turn around time of both the dynamic stress simulation and the fatigue life analysis.

A unique feature of the frequency domain approach is that an analytical model of the structural component can be used to predict the fatigue life of the structural component in terms of specific design parameters of the structural component. This feature is what makes the frequency domain approach widely used in the automotive industry. Unfortunately, all the existing frequency domain approaches focus only on identifying the points of higher stress and predicting the ultimate fatigue life of the component. Therefore, there is a need in the industry for a method of identifying the points of a structural component which are most susceptible to fatigue damage and predicting the ultimate fatigue life of the structural component as well as providing insight on how specific design parameters of the structural component can be changed to increase the fatigue life of the structural component. The relationship between the fatigue life and the specific design parameters of the structural component are described and quantified by the sensitivity of the fatigue life of the structural component with respect to the particular design parameters.

DETAILED DESCRIPTION OF THE INVENTION

The following description of the preferred embodiment of the invention is not intended to limit the scope of the invention to this preferred embodiment, but rather to enable any person skilled in the art to make and use the invention.

Figure 1:
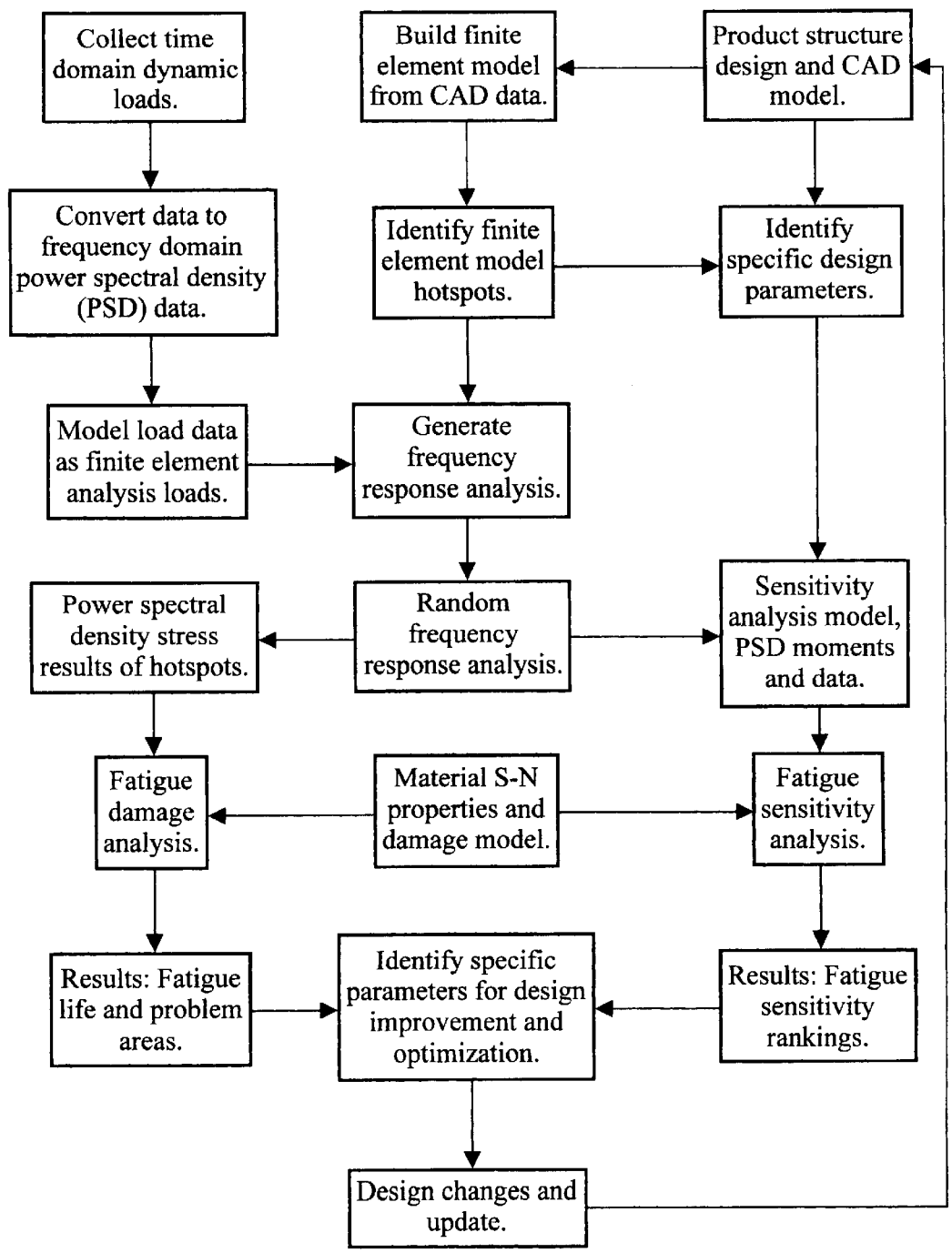
FIG. 1 is a flow chart summarizing the method of the present invention.

Referring to FIG. 1, a flow chart illustrates the method of the present invention. First, an excitation loading profile for a structural component under random process is obtained. Preferably, the excitation profiles are measured as time trace data and obtaining the excitation profile includes transforming the time traces into frequency domain data using a fast Fourier transform (FFT) algorithm. In the preferred embodiment, the structural component is a component of an automotive vehicle, although it is to be understood, that the method of the present invention could be practiced on any structural component exposed to random loading and stress. Preferably, the excitation profile is obtained by driving the automotive vehicle on a road surface. The excitation profile is collected through sensors mounted onto the structural component. The sensors will collect road load-data as the structural component is exposed to the random road surface that are transferred to the structural component through the automotive vehicle.

Irregularities in the road surfaces that a vehicle travels upon are random in nature. It has been established that most of the road surface irregularities are normally distributed and can be described by a stationary random process. For a stationary ergodic random phenomenon, the ensemble averages are equal to the time averages. The statistical properties of a stationary ergodic process can then be computed from a single time history of a sufficiently long period.

A correlation function is a measure of the similarity between two random quantities in a time domain $\tau$. A random process is described in frequency domain in terms of power spectral density (PSD) functions. It can be shown that the power spectral density functions are related to the correlation functions by Fourier transform pairs.

The equations of motion of a linear structural system, in general, are expressed in matrix format. The system of time domain differential equations is usually solved directly in the physical coordinate system corresponding to each load-time step.

The system of time domain differential equations of motion of the structure can be, using the Fourier transform, reduced to a system of frequency domain algebraic equations known as the frequency response equation:

$$[S_x(\omega)]_{nxn} = [H(\omega)]_{nxm}[S_p(\omega)]_{mxm}[H(\omega)]_{mxn}^T.$$

where n is the number of output response variables and $[H(\omega)]^T$ denotes the transpose of a matrix. $[H(\omega)]$ is the transfer function matrix between input loadings and output response variables such as displacement, velocity, acceleration, stress, etc, and is defined as:

$$[H(\omega)] = (-[M]\omega^2 + i[C]\omega + [K])^{-1}.$$

When the multiple input loads are random in nature, a matrix of loading power spectral density functions is generated by employing Fourier transform of a load vector {p(I)}. From the properties of the cross PSD's it is shown that the multiple input PSD matrix is a Hermitian matrix. The random response variables $[S_x(\omega)]$, such as displacement, acceleration and stress response, in terms of the power spectral density functions are obtained by solving the system of linear equations in term of the frequency response.

Next, a relationship is established between the stress profile and the fatigue life of the structural component. An analytical representation of the structural component is created in order to identify areas of the structural component most susceptible to fatigue damage and to predict the fatigue life of the structural component. There are some basic assumptions upon which the analytical model is based. The material behavior for fatigue is described by an S—N curve which has the following form:

$$C=NS_A^m$$

Where $S_A$ denotes the stress amplitude level, N represents the mean number of cycles to failure, and m and C are material constants. The Miner's Rule, which assumes fatigue damage can be accumulated linearly applies. A random process damage model for a Rain Flow counting algorithm is used for stress cycles in a wide-band loading process. Random loading is assumed to be stationary. The spectral density function associated with any stationary process with a zero mean is given as S(f), where f represents the frequency in hertz. The development does not take into account any environmental effects, such as temperature, humidity, etc, and the material constants m and C are assumed to remain unchanged. Preferably, the analytical representation is a finite element model of the structural component. Normal modal and frequency response analyses of the finite element model will allow identification of specific design parameters that will affect the fatigue life of the component.

In the frequency domain, fatigue damage of structures is estimated based upon the statistical properties of the response stress PSD function. The statistical characteristics of the response stress PSD can be obtained through the moments of the PSD function. The $n^{th}$ spectral moment of the stress PSD function S(f), where the frequency f is given in units of hertz, is defined by the following equation:

$$M_n = \int_0^\infty f^n S(f) df$$

The material fatigue properties are preferably measured as an S—N curve, which defines the relationship between the stress amplitude levels, $S_A$, versus the mean cycles to failure, N. For most high cycle fatigue problems ($N \geq 10^4$), the S—N curve can be expressed in simplified form:

$$C=NS_A^m$$

where C and m are the material properties varying with loading an environment conditions, such as mean stress, surface finishing and temperature.

The accumulated damage due to fatigue random loading is evaluated based upon the Palmgren-Miner rule. Using the S—N curve an accumulative damage equation giving the fatigue damage from random stress response can be developed. By setting the accumulated damage equal to unit 1, the time to fatigue failure due to random loading can be readily computed.

Methods have been developed to estimate the fatigue damage by using a different definition of the probability density function, $p(S_A)$. The function p(SA) is usually defined as a function of statistical parameters of the response stress PSD such as $f_0$, $n_0$, $\alpha$ and the $n^{th}$ spectral moment. A generic form of the accumulated fatigue damage, E[AD], takes the form:

$$E[AD]=F(M_n,P_k)$$

where $M_n$ are the $n^{th}$ spectral moment and $P_k$ stands for the $k^{th}$ parameter in the fatigue damage model. In other words, the accumulated fatigue damage is expressed as a function of the spectral moments of the response spectral density function and the parameters in the fatigue damage model. The most popular damage estimating methods are based on a narrow band method. The narrow band approach assumes that the $P(S_A)$ is a Rayleigh distribution. A method known as Wirsching's method is a modification on the narrow band method which includes a correction factor for a wide band process. Take the Wirching's model as an example. The Wirsching's model can be expressed as:

$$E[AD]_{wB} = \lambda(\alpha, m) \frac{Tf_0}{C} (\sqrt{2}\sigma)^m \Gamma\left(\frac{m}{2}+1\right)$$

where $$\lambda(\alpha,m)=(0.926-0.033m)+(0.033m+0.074)(1-\sqrt{1-\alpha})^{(1.587m-2.323)}$$

is an empirical correctional factor, $\Gamma(\cdot)$ is the Gamma function, $f_0$ represents the expected rate of level crossing with positive slope, $\sigma$ is the root mean square of the stress, and $$\alpha = M_2[M_0 M_4]^{-\frac{1}{2}}.$$

Finally, the sensitivity of the fatigue life with respect to the specific design parameters is evaluated, thereby allowing design changes to be made to the structural component to optimize the fatigue life based upon the design parameters to which the fatigue life is most sensitive. The term sensitivity is used to describe the change of the desired objective function when one of several independent variables, such as design parameters ($b_j$, j=1, 2, 3, . . . N), is subjected to change.

Figure 2:
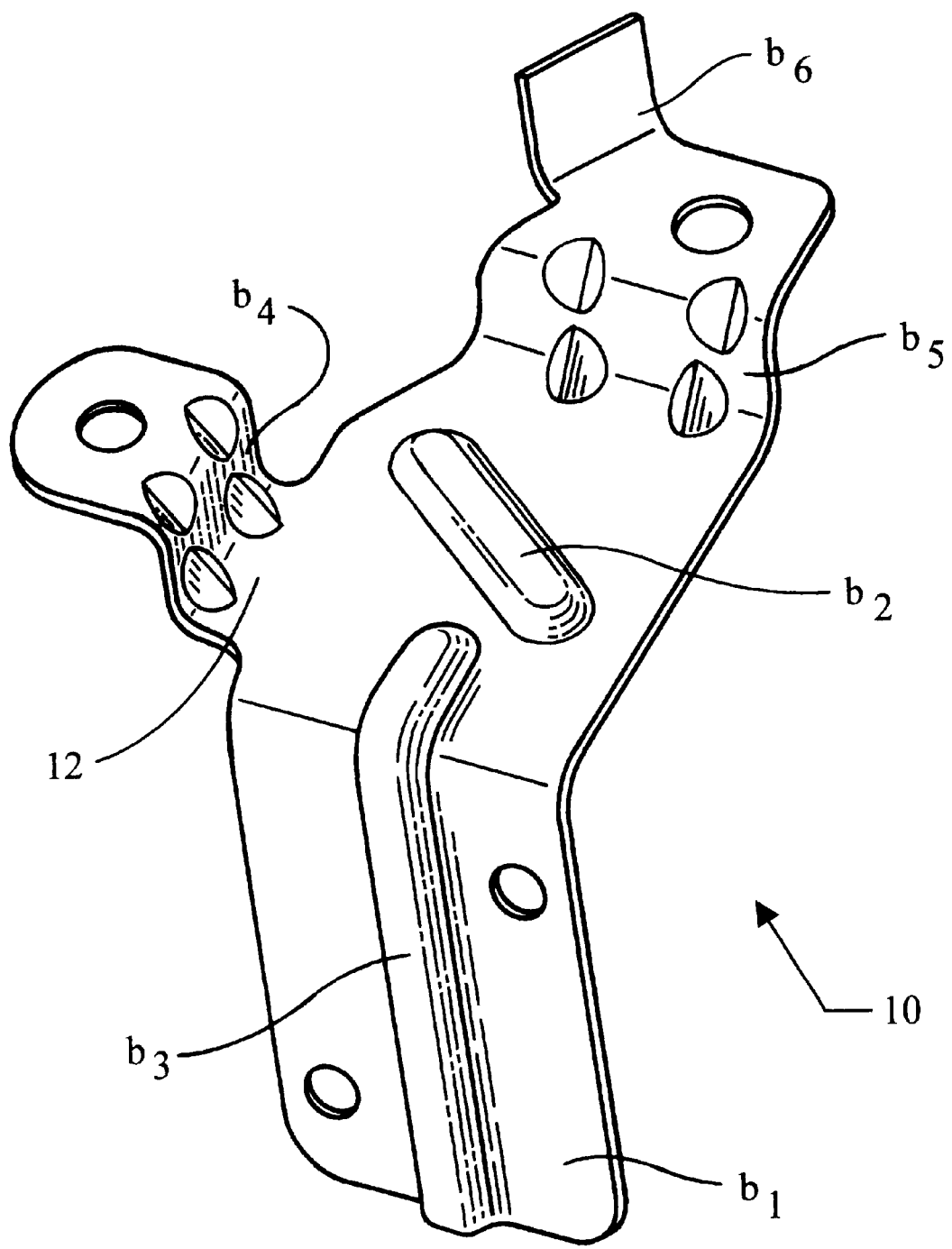
FIG. 2 is a perspective view of a sample component that is to be analyzed using the method of the present invention.

Referring to FIG. 2, an example of a structural component is shown generally at 10. The structural component includes a stress hot-spot 12 which is where the component 10 is most likely to fail under fatigue loading. The structural component 10 also includes six design parameters $b_1$, $b_2$, $b_3$, $b_4$, $b_5$, $b_6$. Adjustment of any of the design parameters $b_1$, $b_2$, $b_3$, $b_4$, $b_5$, $b_6$ will result in a change in how he hot-spot 12 responds to fatigue loading and therefore affects the fatigue life of the component 10. The design parameters $b_1$, $b_2$, $b_3$, $b_4$, $b_5$, $b_6$ of the component 10 shown in FIG. 2 are the thickness of the material at each respective point. The component 10 is a bracket which is used for support. The object of the analysis using the method of the present invention is to determine which of the six identified design parameters will have the greatest impact on how the hot-spot 12 will respond to fatigue loading. In other words, the method of the present invention will determine the sensitivity of the fatigue life of the component 10 relative to the six design parameters $b_1$, $b_2$, $b_3$, $b_4$, $b_5$, $b_6$.

As shown previously, the accumulative damage is an implicit function of the $n^{th}$ spectral moments such as $M_0$, $M_2$, $M_4$. Therefore, the task of evaluating the sensitivity of the accumulated damage is actually the evaluation of the sensitivity of the $n^{th}$ spectral moments. The generic formula for the sensitivity of the accumulated fatigue damage with respect to a particular design parameter, bj, takes the form:

$$\frac{\partial(E[AD])}{\partial b_j} = G\left(M_n, P_k, \frac{\partial M_n}{\partial b_j}, \frac{\partial P_k}{\partial b_j}\right)$$

In other words, the sensitivity of the accumulated fatigue damage with respect to design parameter bj can be expressed in terms of the spectral moments, $M_n$, the parameters, $P_k$, the sensitivities of the spectral moments, $$\frac{\partial M_n}{\partial b_j},$$

and the sensitivities of the parameters, $$\frac{\partial P_k}{\partial b_j}.$$

Many models can be used to calculate these sensitivities, one such model is described herein, where $P_k$ are constants. The sensitivity of the nth spectral moments, based on Equation Fifteen, can be expressed as:

$$\frac{\partial M_n}{\partial b_j} = \frac{\partial}{\partial b_j} \int_0^\infty f^n S_x(f) df$$

$$= \frac{\partial}{\partial b_j} \int_0^\infty f^n S_p(f) |H_p(f)|^2 df$$

$$= 2 \int_0^\infty f^n S_p(f) |H_p(f)| \frac{\partial |H_p(f)|}{\partial b_j} df$$

where $|H_p(f)|$ represents the magnitude of frequency response of the stress and $$\frac{\partial |H_p(f)|}{\partial b_j}$$

is the sensitivity of frequency response with respect to the design parameter $b_j$.

Using the Wirsching's model as an example, the sensitivity of the expected rate of level crossing with positive slope ($f_0$) can be obtained by taking the partial derivative of $f_0$ with respect to the design parameter $b_j$:

$$\frac{\partial f_0}{\partial b_j} = \frac{f_0}{2}\left(\frac{1}{M_2}\frac{\partial M_2}{\partial b_j} - \frac{1}{M_0}\frac{\partial M_0}{\partial b_j}\right)$$

Therefore, the sensitivity of $f_0$, the expected up-crossing frequency, can be expressed in terms of $M_0$, $M_2$ and their associated sensitivities.

An irregularity factor, $\alpha$, of the resultant spectral density function, $Sp(f)$, is defined as the ratio of the up-crossing rate to the peak rate. The sensitivity of $\alpha$ can be expressed as:

$$\frac{2\alpha}{2b_j} = \alpha\left(\frac{1}{M_2}\frac{\partial M_2}{\partial b_j} - \frac{1}{2M_0}\frac{\partial M_0}{\partial b_j} - \frac{1}{2M_4}\frac{\partial M_4}{\partial b_j}\right)$$

whereby the sensitivity of the irregularity factor can be expressed in terms of $M_0$, $M_2$, $M_4$ and their associated sensitivities.

A correction factor, $\lambda$, is an empirical representation of the rain flow counting process. The sensitivity of $\lambda$ with respect to the design parameters $b_j$ can be expressed as:

$$\frac{\partial \lambda}{\partial b_j} = \frac{ab(1-a)}{\sqrt{1-\alpha^2}}\left(1 - \sqrt{1-\alpha^2}\right)^{b-1}\frac{\partial \alpha}{\partial b_j}$$

where a and b are constants. Therefore, the sensitivity of the correction factor, $\lambda$, which serves as the correction factor for the rain flow counting process, can be evaluated using the sensitivity of the irregularity, $\alpha$. Moreover, the sensitivity of $\alpha$ can be obtained by using the sensitivities of M0, M2 and M4.

The sensitivity of the accumulative damage for the narrow band process can be evaluated as follows:

$$\frac{\partial E[AD]_{NB}}{\partial b_j} =$$

$$\frac{\partial}{\partial b_j}\left(\frac{f_0}{B}\Gamma\left(\frac{m}{2}+1\right)(2M_0)^{m/2}\right) = \frac{E[AD]_{NB}}{2}\left(\frac{1}{M_2}\frac{\partial M_2}{\partial b_j} + \frac{m-1}{M_0}\frac{\partial M_0}{\partial b_j}\right)$$

Therefore, the sensitivity of the narrow band cumulative damage can be related to the sensitivity of $M_0$ and $M_2$.

The sensitivity of the accumulative damage for the wide band process can be expressed as:

$$\frac{\partial E[AD]_{WB}}{\partial b_j} = \frac{\partial}{\partial b_j}(\lambda E[AD]_{NB})$$

$$= \left(\frac{\lambda}{2}\left(\frac{1}{M_2}\frac{\partial M_2}{\partial b_j} + \frac{m-1}{M_0}\frac{\partial M_0}{\partial b_j}\right) + \frac{\alpha b}{\sqrt{1-\alpha^2}}(1-a)\left(1-\sqrt{1-\alpha^2}\right)^{b-1}\frac{\partial \alpha}{\partial b_j}\right)E[AD]_{NB}$$

in which the sensitivity of the wide band cumulative damage is a combination of the sensitivities of the correction factor, $\lambda$, and the narrow band cumulative damage, E[AD], both of which are functions of $M_0$, $M_2$, $M_4$ and their associated sensitivities.

Once the sensitivities of the fatigue life with respect to the specific design parameters are identified, they are then ranked to identify the most sensitive and critical design parameters. These parameters can be studied, and design modifications can be made by making changes to the most significant design parameters to increase the fatigue life of the component. A new finite element model of the component with the design changes can be analyzed as described above to further identify significant design parameters and to further optimize the design of the component.

The foregoing discussion discloses and describes one preferred embodiment of the invention. One skilled in the art will readily recognize from such discussion, and from the accompanying drawings and claims, that changes and modifications can be made to the invention without departing from the true spirit and fair scope of the invention as defined in the following claims. The invention has been described in an illustrative manner, and it is to be understood that the terminology which has been used is intended to be in the nature of words of description rather than of limitation.

We claim:

1. A method for determining the sensitivity of the fatigue life of a structural component with respect to specific design parameters comprising:

obtaining an stress profile for a structural component under random excitation;

establishing a relationship between the stress profile and the fatigue life of the structural component by creating an analytical representation of the structural component to identify areas of the structural component most susceptible to fatigue damage and to predict the fatigue life of the structural component;

developing the sensitivity of the fatigue life with respect to the specific design parameters to determine which design parameter has the most significant impact upon the fatigue life of the component; and calculating a frequency response equation for a power spectral density response and using the frequency response equation and the power spectral density response to identify high stress levels in the structural component to identify areas of the structural component most susceptible to fatigue damage.

2. The method of claim 1 including optimizing the design of the structural component based upon the design parameters to which the fatigue life is most sensitive.

3. The method of claim 1 wherein the analytical representation of the structural component is a finite element model.

4. The method of claim 1 wherein obtaining the stress profile for a structural component under random process includes measuring he stress profiles as time traces and transforming the time traces into frequency domain data using a fast Fourier transform algorithm.

5. The method of claim 4 further comprising driving an automotive vehicle on a road surface and wherein obtaining a stress profile includes obtaining an excitation profile for a structural component of the automotive vehicle under random process to the structural component from the road surface.

6. The method of claim 1 including calculating an accumulative damage equation and using the accumulative damage equation to predict fatigue life of the structural component.

7. The method of claim 6 wherein developing the sensitivity of the fatigue life with respect to design parameters includes identifying design parameters associated with the structural component and determining the sensitivity of the frequency response equation and the power spectral density equation with respect to the identified design parameters.

8. The method of claim 7 including determining the sensitivity of the accumulative damage equation with respect to the identified design parameters to determine the sensitivity of the fatigue life of the component with respect to each of the identified design parameters.

9. A method for determining the sensitivity o the fatigue life of a structural component with respect to specific design parameters comprising:

collecting time domain dynamic loads in terms of stationary random process data;

converting the time domain load data into the frequency domain data in terms of power spectral density functions by using a fast Fourier transformation technique;

modeling the power spectral density load data as finite element analysis loads;

building a finite element model based on structural design of the component and computer aided designs of the component;

identifying finite element model hotspots using normal modal analysis;

identifying specific design parameters for fatigue sensitivity determination based upon design parameters and component hotspots;

generating a frequency response model for finite element analysis;

perform random frequency response analysis;

perform fatigue damage analysis based upon the power spectral density stress results, the material fatigue S—N properties and the damage model;

establish a sensitivity analysis model and stress power spectral density moments and data;

perform structural fatigue sensitivity analysis based on the sensitivity analysis model, the material fatigue S—N properties and the damage model;

rank the fatigue sensitivity results with respect to the identified specific design parameters;

identify the most sensitive and critical design parameters for design improvements and optimization.

* * * * *

UNITED STATES PATENT AND TRADEMARK OFFICE
CERTIFICATE OF CORRECTION

PATENT NO.     : 6,704,664 B2
DATED          : March 9, 2004
INVENTOR(S)    : Hong Su et al.

Page 1 of 1

It is certified that error appears in the above-identified patent and that said Letters Patent is hereby corrected as shown below:

Column 7,
Line 3, after "measuring" delete "he" and substitute -- the -- in its place.

Column 8,
Line 1, after "sensitivity" delete "o" and substitute -- of -- in its place.

Signed and Sealed this

Seventeenth Day of August, 2004

JON W. DUDAS
*Acting Director of the United States Patent and Trademark Office*